(12) United States Patent
Naboulsi

(10) Patent No.: US 6,731,925 B2
(45) Date of Patent: May 4, 2004

(54) SAFETY CONTROL SYSTEM FOR VEHICLES

(76) Inventor: Mouhamad Ahmad Naboulsi, 5517 Crispen Ct., West Bloomfield, MI (US) 48323

( * ) Notice: Subject to any disclaimer, the term of this patent is extended or adjusted under 35 U.S.C. 154(b) by 0 days.

(21) Appl. No.: 10/287,299

(22) Filed: Nov. 4, 2002

(65) Prior Publication Data

US 2003/0096594 A1 May 22, 2003

Related U.S. Application Data

(63) Continuation-in-part of application No. 10/279,447, filed on Oct. 24, 2002, now abandoned.
(60) Provisional application No. 60/336,293, filed on Oct. 24, 2001, and provisional application No. 60/390,877, filed on Jun. 21, 2002.

(51) Int. Cl.[7] .................................................. H04B 1/38
(52) U.S. Cl. ................... 455/345; 455/569.2; 340/575; 340/576
(58) Field of Search ............................... 455/345, 411, 455/565, 567, 569.1, 569.2, 575.9, 556.1, 557; 340/525, 575, 576, 901, 438, 441

(56) References Cited

U.S. PATENT DOCUMENTS

| | | | |
|---|---|---|---|
| 4,485,375 A | 11/1984 | Hershberger | 340/576 |
| 5,266,922 A * | 11/1993 | Smith et al. | 455/575.9 |
| 5,897,505 A | 4/1999 | Feinberg et al. | 600/547 |
| 6,085,078 A | 7/2000 | Stamegna | 455/345 |
| 6,085,278 A | 7/2000 | Gates et al. | 710/263 |
| 6,104,101 A | 8/2000 | Miller et al. | 307/10.1 |
| 6,107,922 A | 8/2000 | Bryuzgin | 340/576 |
| 6,114,949 A | 9/2000 | Schmitz et al. | 340/425.5 |
| 6,147,315 A | 11/2000 | Rudolph et al. | 200/61.54 |
| 6,148,251 A | 11/2000 | Downs | 701/36 |
| 6,154,123 A | 11/2000 | Kleinberg | 340/436 |
| 6,154,658 A | 11/2000 | Caci | 455/466 |
| 6,188,315 B1 | 2/2001 | Herbert et al. | 340/438 |
| 6,209,767 B1 | 4/2001 | Liou | 224/276 |
| 6,240,347 B1 | 5/2001 | Everhart et al. | 701/36 |
| 6,246,933 B1 | 6/2001 | Bague | 701/35 |
| 6,249,720 B1 | 6/2001 | Kubota et al. | 701/1 |
| 6,253,131 B1 | 6/2001 | Qugley et al. | 701/36 |
| 6,256,558 B1 | 7/2001 | Sugiura et al. | 701/1 |
| 6,263,190 B1 * | 7/2001 | Mamori et al. | 455/569 |
| 6,292,719 B1 | 9/2001 | Seto et al. | 701/1 |
| 6,308,115 B1 | 10/2001 | Yamaguchi et al. | 701/1 |
| 6,335,689 B1 | 1/2002 | Mine | 340/576 |
| 6,339,700 B1 | 1/2002 | Tsai | 455/90 |
| 6,353,778 B1 | 3/2002 | Brown | 701/1 |
| 6,373,472 B1 | 4/2002 | Palalau et al. | 345/173 |
| 6,418,362 B1 | 7/2002 | St. Pierre et al. | 701/36 |
| 6,430,488 B1 | 8/2002 | Goldman et al. | 701/36 |
| 6,434,450 B1 | 8/2002 | Griffin, Jr. et al. | 701/1 |
| 6,434,459 B2 | 8/2002 | Wong et al. | 701/36 |
| 6,438,465 B2 | 8/2002 | Obradovich et al. | 701/1 |

OTHER PUBLICATIONS

DaimlerChrysler 300–M IT–Edition brochure, date unknown.

* cited by examiner

Primary Examiner—Quochien B. Vuong
(74) Attorney, Agent, or Firm—Gifford, Krass, Groh, Sprinkle, Anderson & Citkowski, P.C.

(57) ABSTRACT

A safety control system for vehicles including a telephone and sensors for sensing a potentially dangerous condition and for automatically disabling the telephone when sensing such condition. The sensors include two sensors mounted on a steering member to be gripped by the two hands of the driver of the vehicle and effective to disable an operation of the telephone when the two hands of the driver are not sensed as gripping the steering member while the vehicle is in motion. The sensors may also disable the telephone, and/or actuate a signaling device, when sensing other driver conditions or vehicle conditions in which the distraction of the driver by a telephone conversation could increase the risk of accidents.

45 Claims, 4 Drawing Sheets

SAFETY CONTROL SYSTEM FOR VEHICLES

RELATED APPLICATIONS

The present application is a continuation-in-part of U.S. patent application Ser. No. 10/279,447, filed Oct. 24, 2002, Abandoned which claims the priority dates of Provisional Application No. 60/336,293 filed Oct. 24, 2001, and Provisional Application No. 60/390,877 filed Jun. 21, 2002, the contents of which are incorporated herein by reference.

FIELD OF THE INVENTION

The present invention relates to the field of telematics, namely to the field of integrating information, communication, computing and entertainment technologies into vehicles for civilian or military use. The invention particularly relates to safety control systems for vehicles for avoiding potentially dangerous conditions tending to produce accidents.

BACKGROUND OF THE INVENTION

One potentially dangerous condition is the use of a vehicle telephone by the vehicle driver while driving the vehicle. The use of telematics in general and particularly cellular telephones by drivers while driving has been found to increase the possibility of an accident since such a telephone not only diverts the driver's attention from driving, but also generally requires the use of at least one of the driver's hands and distract the driver's eyes from the road and traffic. In fact, many states and countries have enacted legislation requiring that telephones used in vehicles by drivers while driving must be of the "hands free" type and usually telematics equipment carries a warning to educate and discourage the driver about the risk of using while driving. However, such legislation is difficult to enforce and education is not usually effective in assuring driver compliance. Moreover, even where the vehicle is equipped with a "hands free" telephone, drivers nevertheless still frequently use one hand for holding or dialing the telephone. When one hand is occupied by holding a telephone, the danger of causing an accident in an emergency situation is increased because of the additional reaction time required to properly grip the steering wheel with both hands.

There are other potentially dangerous conditions and inherent risks in driving that depends on the driving act itself, such as accelerating, decelerating, excessive maneuvering, merging to or exiting a freeway, passing, changing lanes, changing gears, depressing the clutch, high speed, negotiating a turn, braking, reverse-driving, or a stress condition on the part of the driver, which could increase the possibility of an accident should the driver be distracted by the telephone. This inherent risk is also dependent on the driving purpose as well, for example, the risk in driving a police cruiser is inherently riskier then in driving a sedan, and driving a delivery van has different risk than driving the family van.

Herbert et al., U.S. Pat. No. 6,188,315 and Brown, U.S. Pat. No. 6,353,778, disclose systems for avoiding preset potentially dangerous conditions while operating a vehicle having a vehicle telephone, but the systems described in those patents are of relatively limited application, and do not provide for avoiding dangerous conditions or to managing risk and individualizing the warnings to individual driving skills or application and to combinations of events and environmental conditions.

OBJECTS AND BRIEF SUMMARY OF THE INVENTION

An object of the present invention is to provide a safety control system for vehicles tending to reduce the possibility of accidents in one or more of the above respects. Another object of the invention is to provide a method of avoiding potentially dangerous conditions while operating a vehicle.

According to one aspect of the present invention, there is provided a safety control system for vehicles including a telephone and sensor means for sensing a potentially dangerous condition and for automatically disabling the telephone when sensing such condition; characterized in that the sensor means includes two sensors mounted on a steering member to be gripped by the two hands of the driver of the vehicle and effective to suspend use of the telephone when the two hands of the driver are not sensed as gripping the steering member while the vehicle is in motion. This system is modular, dynamic, interactive, and adaptive to each individualized user. The invention employs a method for automated machine prioritizing to provide assistance the to driver and to optimize the functionality of telematics features accessibility by arranging them according to a user's needs and preferences in the operation based on usage frequency of individual features and/or application or as customized individually by the user preferences, skills and events.

According to further features in the described preferred embodiment, the steering member is a steering wheel, and the sensor means includes two sensors on opposite sides of the steering wheel located to sense the proper gripping of the steering wheel by the two hands of the driver. Preferably, the two sensors are located approximately on or between the "two" and "ten" and the "three" and "nine" clock positions of the steering wheel.

It will thus be seen that such a system, requiring both hands to be on the steering wheel in order for the driver to operate the telephone/telematics, not only requires the vehicle to be equipped with a "hands free" telephone/telematics system, or a telephone/telematics system that can be used as such with an adapter or when docked to the system gateway, but also enforces the use of the "hands free" feature by sensing that the driver actually has both hands placed on the steering member before the telephone or other telematics can be operated. Disabling the operation of the telephone would preferably include not only disabling making outgoing and receiving incoming telephone calls, but also disabling the ringing signal of an incoming call since such a ringing signal could be particularly distracting to the driver in a critical situation.

According to further features in the described preferred embodiment, the vehicle may also include a computer or the driver may also use a portable multi-function telematics device in the vehicle allowing access to the Internet for transmitting and/or receiving faxes or e-mail or browsing the web or accessing a WAN, the sensor means also disabling driver initiated access when the two hands of the driver are not sensed as gripping the steering member while the vehicle is in motion.

In most cases, the steering member would be a steering wheel as presently included in conventional vehicles. However, in certain applications the steering member could be a joystick, or other type of steering member. In such case, the sensors are placed in areas a driver is recommended or required to grip the steering member to safely control the vehicle.

According to further optional features in the preferred embodiment of the invention described below, the sensor means may further include means for sensing accelerating, decelerating, merging to or exiting a freeway, passing, changing lanes, changing gears, depressing the clutch a reverse-drive condition of the vehicle, the braking of the vehicle, the undue proximity of the vehicle to another vehicle, excessive maneuvering, and/or an unduly high velocity of the vehicle, any one of which conditions, or combination of conditions, may also be effective to disable the operation of the telephone, computer, or other potentially distracting equipment within the vehicle.

According to still further optional features in the preferred embodiment of the invention described below, at least one of the sensors on the steering member also senses a physiological condition of the driver and disables the telephone when a predetermined physiological condition is sensed. For example, the physiological conditions sensed could be a predetermined gripping force applied by a hand of the driver while gripping the steering wheel, or a predetermined pulse rate, temperature, blood pressure, and/or skin conductivity of the driver. Such physiological condition may indicate a stress condition of the driver and, when sensed, disable the incoming operation of the telephone so as not to aggravate the stressed condition.

The system may also include means for indicating a drowsiness condition. For example, the system may include a steering direction sensor which actuates a drowsiness alarm when sensing a failure to change the steering direction within a predetermined time, distance interval while accounting for vehicle speed in indicating a possible drowsiness condition in the driver. Additionally, such sensor when monitored with respect to changes over time will indicate jerk reaction, which indicates that the driver was not paying attention and the system will temporarily suspend all telematics to give the driver a chance to recover. Another application for such a sensor is the monitoring of an OFF Zero angle for an extended period of time/distance which can indicate a blind curve or hard curve, and again, here the system will temporarily suspend telematics of all functions from interacting with the driver and vice versa until normal driving functions are restored.

According to another aspect of the present invention, there is provided a method of avoiding potentially dangerous conditions while operating a vehicle having a telephone and a steering mechanism including a steering member to be manipulated by the driver, comprising: providing the steering member with two sensors for sensing the gripping of the steering member by the two hands of the driver; and disabling the telephone when the two sensors fail to sense the gripping of the steering member by both hands of the driver while the vehicle is in motion.

According to further features in the described preferred embodiment, the telephone may also be disabled when the vehicle is traveling in the reverse direction, or is being braked, or is within a predetermined proximity of another vehicle, or is traveling at a high velocity accelerating, decelerating, merging to or exiting a freeway, passing, changing lanes, changing gears, depressing the clutch, or a driver is occupied using other accessories in the vehicle. Since a high degree of attention of the driver is required under all the foregoing conditions, operation of the vehicle telephone, even the ringing signal of an incoming telephone call, could be highly distracting to the driver and is therefore disabled to avoid the possibility of increasing the risk of an accident.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENT

Figure 1:
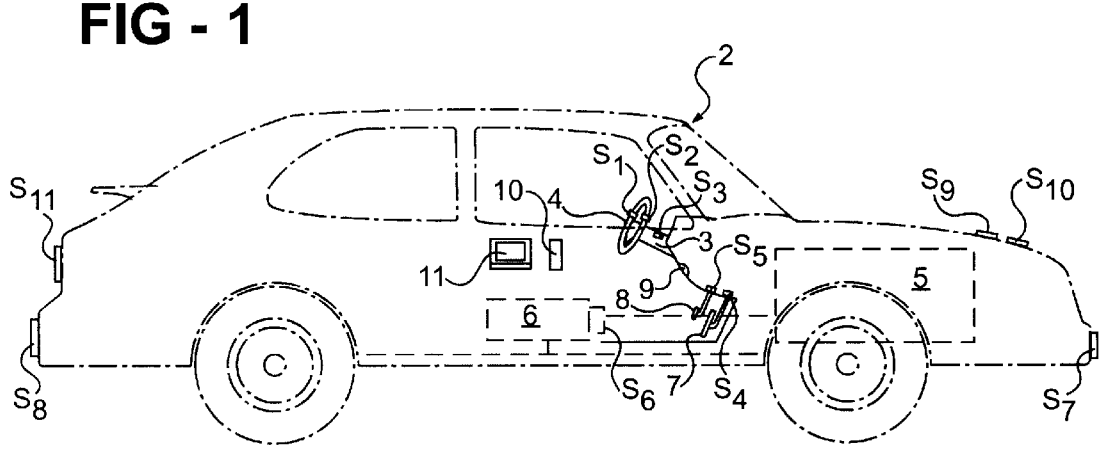
FIG. 1 schematically illustrates one form of safety control system for vehicles constructed in accordance with the present invention.

FIG. 1 schematically illustrates a vehicle, generally designated 2, equipped with a control system for sensing a variety of risk factors and potentially dangerous conditions and for automatically executing various responses when sensing such conditions in order to avoid hazardous situations tending to increase the possibility of an accident. A particularly hazardous situation avoided by the control system illustrated in FIG. 1 is the use of the vehicle telephone or other telematics such as e-mail, incoming page or the like in certain situations wherein a making of a telephone call by the vehicle driver, or the receiving of an incoming call, particularly the ringing current of such a call, may be so distracting to the driver as to increase the possibility of an accident in the event the driver is in a high-risk driving situation. In such cases, the vehicle telephone and other telematics are suppressed and no incoming telematics are allowed to distract the driver. In case the driver is the party initiating the telematics, a visual indicator and audio feedback is activated to indicate to the driver that telematics is disabled and supply reason and recommend driving modification to enable telematics. Another condition sensed by the system is undue stress in the driver, as indicated by the sensed pulse rate, temperature, blood pressure, skin conductivity (e.g. perspiration), loud voice(s) or stressful sounds in the cabin, such as baby crying, dog barking etc., any combination of one or more of which conditions would also disable incoming telematics. A further condition sensed by the system is the possibility of drowsiness on the part of the driver, in which case an audio alarm would be activated to alert the driver to this condition. Other alarms to overcome driver drowsiness would include vibration in the seat, changing HVAC temperature settings and blower speed to extremes, etc. The system will restore telematics when conditions are normalized and will notify driver of all missed activities.

Vehicle 2 illustrated in FIG. 1 is a conventional vehicle including a steering mechanism, generally designated 3, having a steering wheel 4, a propulsion device such as a motor or engine 5 for driving the vehicle via a transmission or other torque converting means schematically indicated 6, an acceleration pedal 7, and a braking pedal 8 for controlling the vehicle. Vehicle 2 further includes one or more visual indicator and audio alarms 9, e.g. mounted within the forward-look ahead viewing or hearing by the driver.

FIG. 1 further schematically illustrates a cellular telephone 10 within the vehicle, and a computer 11 or other multifunction telematic device allowing access to the Internet for transmitting and/or receiving faxes or e-mail, WAN and Web access. Vehicle 2 illustrated in FIG. 1 may also include many other components conventionally provided on vehicles at the present time or to be provided in the future.

The safety control system included in vehicle 2 illustrated in FIG. 1 includes a plurality of sensors for sensing various conditions with respect to the vehicle driver and/or the vehicle itself. These signals are collected via direct taping to existing or added sensors or via vehicle bus and user specified values. These include sensors $S_1$ and $S_2$ applied to the steering wheel 4 of the vehicle; sensor $S_3$ applied to the steering mechanism 3 of the vehicle to sense changes in the steering direction; sensor $S_4$ sensing the condition of the gas pedal 7; sensor $S_5$ sensing the condition of the braking pedal 8; and sensor $S_6$ sensing the condition of the transmission or other type torque converter 6.

Also schematically illustrated in FIG. 1 are sensors $S_7$ and $S_8$ carried to sense the proximity of the vehicle with respect to another vehicle; sensor $S_9$ sensing darkness or alternatively sensing the activation of the headlight; and sensor $S_{10}$ sensing rain or alternatively sensing the activation of the front or rear wipers or headlight wipers.

As will be described more particularly below, the foregoing sensors (or signals) are generally effective only when the vehicle is moving to sense their respective conditions and to execute certain control functions in order to decrease the possibility of an accident. One important control function is to disable an incoming call from ringing the telephone 10, and the computer or other telematics portable or built in 11 from accessing the Internet or announcing incoming signals, e.g. page, e-mail etc., and to indicate same by actuating a visual indicator and an audio feedback if a driver attempts to initiate telematics during an unsafe or a high risk condition 9 and may direct a driver to alternative driving habit to gain access to telematics. The system will restore telematics when conditions are normalized and will notify driver of all missed activities. In some cases, such as where a drowsiness condition is sensed, an audio alarm 9 is actuated. Other alarms to overcome driver drowsiness would include vibration in the seat, changing HVAC temperature settings and blower speed to extremes, etc.

Figure 2:
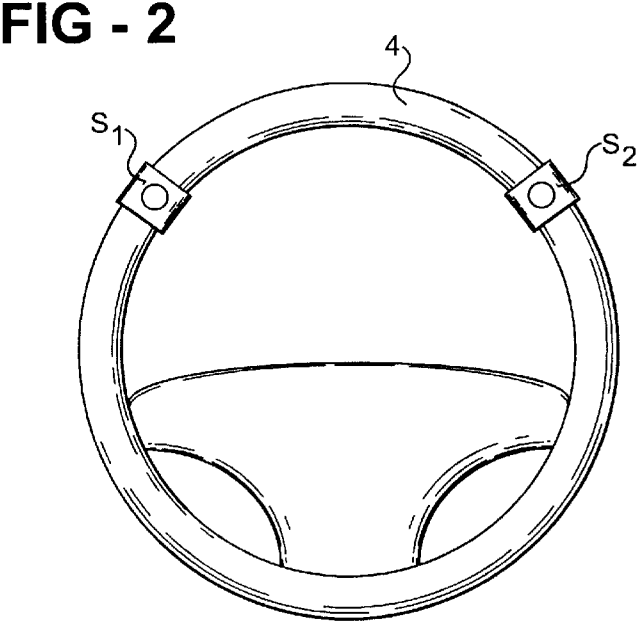
FIG. 2 is an enlarged view illustrating the steering wheel in the vehicle of FIG. 1 and the sensors mounted thereon.

FIG. 2 more particularly illustrates the sensors $S_1$, $S_2$ mounted on the steering wheel 4. As shown in FIG. 2, the two sensors are mounted on or between the "two" and "ten" and the "three" and "nine" clock positions of the steering wheel 4; the "two" and "ten" positions are considered to be the most preferred ones for the two hands of the driver in order to manipulate the steering wheel, but other positions could be employed, such as "nine and fifteen", which provide more clearance for activated airbags. The two sensors $S_1$, $S_2$ thus sense the proper positioning of the two hands of the driver on the steering wheel 4.

The two sensors $S_1$, $S_2$, which may be attached to or embedded in the steering wheel, may be simple electrical switches which are actuated by the respective hand of the driver when properly gripping the steering wheel. Preferably, however, one or both of the sensors $S_1$, $S_2$ or other sensors are also capable of sensing a physiological condition of the driver, such as the gripping force applied by the driver's hand, or the pulse rate, blood pressure, temperature and/or electrical skin conductivity of the driver's hand while gripping the steering wheel. For example, sensor $S_1$ could include a transducer for converting pressure to an electrical signal, such as a spring-type, carbon-type transducer, optical type or semiconductor type. Sensor $S_2$ could include one or more transducers, such as known in finger probes, for sensing pulse rate, temperature, and/or electrical skin conductivity, and for outputting an electrical signal corresponding to the magnitude of the sensed condition, as described for example in U.S. Pat. Nos. 6,319,205; 5,438,986; 5,065,749; 4,860,759; 6,415,176 or 5,897,505, the contents of which are incorporated herein by reference.

As will be described more particularly below, sensors $S_1$ and $S_2$ thus sense that both the driver's hands properly grip both sides of the steering wheel 4 to enable operation of the telephone 10 and the computer 11 or similar multi-function or standalone telematics devices. Thus, the telephone 10 can be permitting "hands free operation" or a telephone/telematics system that can be used as such with an adapter or when docked to the system gateway, as required by-many laws to avoid accidents, but also the driver is permitted to use the telephone only in a "hands free" manner, thereby precluding the driver from gripping a telephone to operate it even though the telephone or the telematics system may has a "hands free" capability.

In addition, by providing sensor $S_1$ and/or sensor $S_2$ with the capability of sensing a physiological condition of the driver while gripping the steering wheel, other conditions can be sensed to disable the telephone for further reducing the possibility of an accident. For example, the gripping force applied by one or both hands of the driver may indicate a stress condition of the driver. A stressed condition may be also indicated by the sensed pulse rate, temperature and/or electrical skin conductivity (the latter indicating perspiration) of the driver. If a stress condition is sensed, the telephone 10 is disabled so as to decrease the possibility that the ringing noise of an incoming telephone call will so distract the stressed driver as to create a hazardous condition, or that the making of an outgoing call by the driver will be so distracting to the stressed driver as to create a hazardous condition.

The provision of a grip sensor on the steering wheel also enables the system to sense drowsiness or dozing of the driver, as in U.S. Pat. No. 4,485,375, incorporated herein by reference. Thus, if the gripping force sensed by sensor $S_1$ and/or sensor $S_2$ drops while the vehicle is in motion, this could indicate a drowsiness condition. If such a condition is sensed, the audio alarm 9, or alternatively a vibrator, may be activated, together with a visual indicator 8, in an attempt to arouse the driver and to alert the driver to the drowsiness condition. When drowsiness is sensed, the telephone 10 would not be disabled since the ringing of an incoming call may be further effective to arouse the driver. Other alarms to overcome driver drowsiness would include vibration in the seat, changing HVAC temperature settings and/or blower speed to extremes, etc.

The sensors $S_1$ and $S_2$ are preferably located at the ten o'clock and two o'clock positions but may be alternatively located in other positions such as the nine o'clock and three o'clock positions. The mechanisms of the switch include a jog switch and slide switch and a rocker switch. The sensors can be arranged to be actuated either in the thumbs-up position or the thumbs-down position. The sensors are tested for integrity by the microprocessor 20 during start up and are designed so as not to be triggered by accidents. The detection of failed switches will cause the microprocessor to block operation of the system.

Sensor $S_3$ is coupled to the steering mechanism 3 so as to sense changes in the steering direction. For example, an alert driver constantly makes minor changes in the steering direction automatically, but not so with respect to a drowsy or dozing driver. Accordingly, if sensor $S_3$ fails to sense a change in the steering direction within a predetermined time interval, this would indicate a possible drowsiness condition in the driver, and therefore the audio alarm 9 would be activated in an attempt to arouse the driver and alert him to that condition. Other alarms to overcome driver drowsiness would include vibration in the seat, changing HVAC temperature settings and blower speed to extremes, etc. or changing recline status or CD tracks and volumes to extremes.

Sensor $S_4$ senses the depression of the gas pedal 7, sensor $S_5$ senses the depression of the brake pedal 8, and sensor $S_6$ senses the condition of the transmission 6 and/or also the velocity of the vehicle. For example, if the transmission is in reverse gear, the driver should not be distracted by receiving or making a telephone call, and therefore the telephone should be disabled. If desired, the same could apply in any gear other than the normal drive gear. Also, if the vehicle is moving at a relatively high velocity, or is engaged in turning or otherwise rapidly maneuvering, such that any unnecessary distraction of the driver should be avoided, the telephone could likewise be disabled.

Sensor $S_7$ mounted at the front of the vehicle senses its proximity to a vehicle ahead of it; sensor $S_8$ mounted at the rear of the vehicle senses the proximity of a vehicle behind it; sensor $S_9$ senses the darkness level of the road on which the vehicle is traveling (e.g., whether day or night, whether the road is brightly illuminated); sensor $S_{10}$ senses a rain condition; and sensor $S_{11}$ senses whether either of the turn indicators of the vehicle is operating to signal for a turn or a change of lanes.

The conditions sensed by sensors $S_7$–$S_{11}$ are also such that a hazard may be produced if, during the existence of such a condition, the full attention of the driver would be diverted by the ringing of the telephone or by the use of the telephone for making an outgoing call. Accordingly, under such conditions, the telephone 10 is disabled from operation. Similarly, the computer 11, if present, is disabled from operation to preclude access to the Internet for transmitting and/or receiving faxes or e-mail, which could also result in a similar distraction increasing the possibility of causing an accident.

Figure 3:
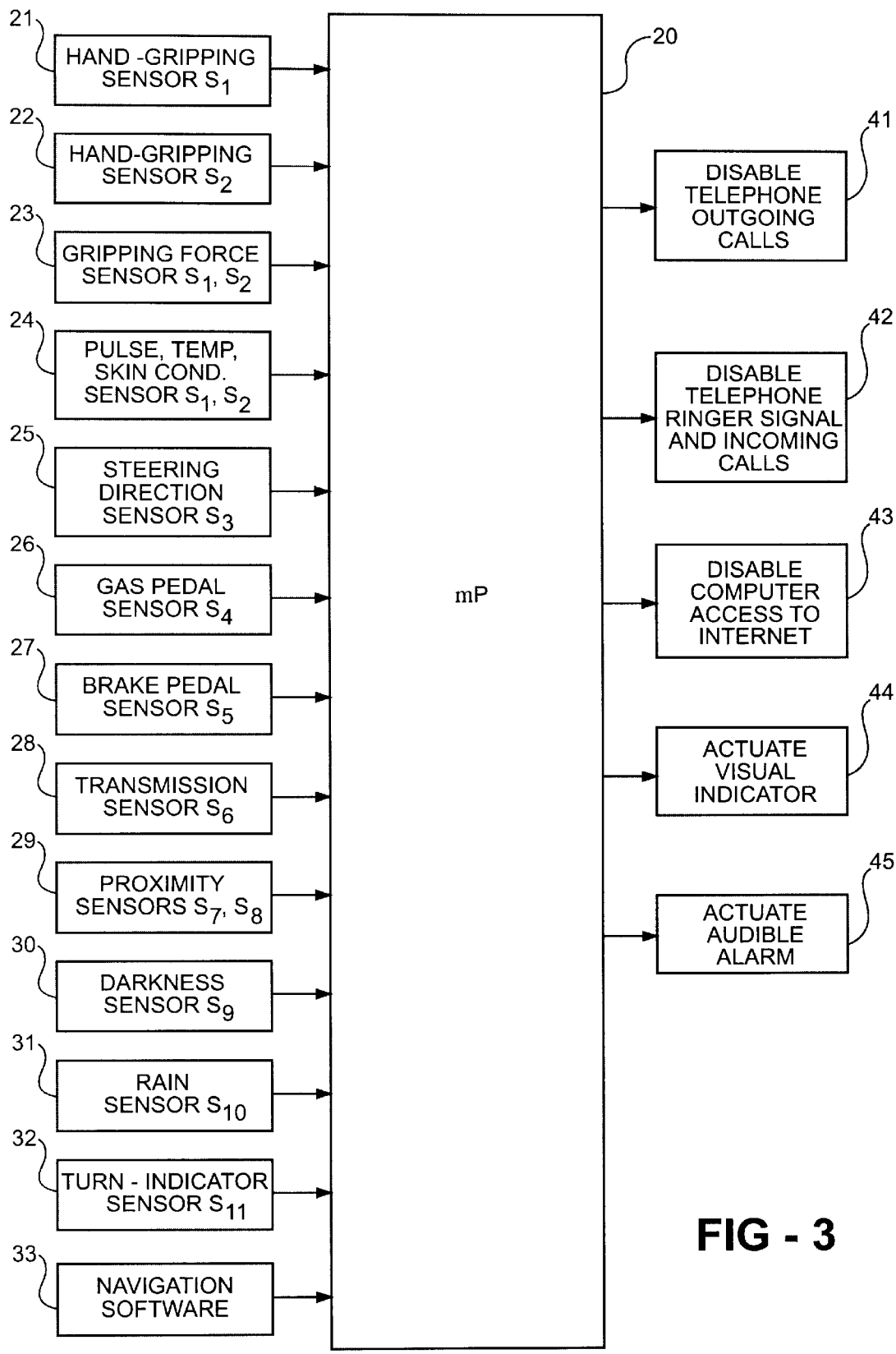
FIG. 3 is a block diagram illustrating the main components in the system of FIG. 1.

FIG. 3 is a block diagram schematically illustrating a microprocessor, generally designated 20, included in the vehicle safety control system of FIG. 1, together with its inputs schematically indicated by block 21–30, and the outputs schematically indicated by blocks 31–35.

Thus, as shown in FIG. 3, microprocessor 20 includes inputs 21 and 22 from the steering wheel sensors $S_1$, $S_2$, to indicate whether the steering wheel is being properly gripped by the two hands of the driver. Microprocessor 20 further includes an input 23 indicating the gripping force applied by one or both of the hands to the sensors $S_1$, $S_2$, and an input 24, also from one or both of the sensors $S_1$, $S_2$, indicating the pulse, skin conductivity, temperature and/or other physiological condition of the driver having a bearing on proneness of the driver to accidents. As indicated earlier, these inputs indicate particularly whether the driver is in a stressed condition, drowsy, or in an alternate embodiment, when an optional breath alcohol sensor is activated.

Another input into microprocessor 20 is from the steering direction sensor $S_3$, as indicated by block 25. This input is helpful in indicating the alertness of the driver, particularly whether the driver may be in a drowsy or even a dozing state, which would be indicated if this input shows no change in the steering direction within a predetermined period of time.

Another input to the microprocessor would be from a sensor associated with the vehicle cup holder to indicate when a cup which was initially disposed in the holder has been removed, as for drinking. The sensor might include a weight indicator to determine whether the cup was empty when lifted or a temperature sensor to sense heated beverages.

Further inputs into microprocessor 20 include signals from the gas pedal sensor $S_4$ to indicate high acceleration (block 26); the braking pedal sensor $S_5$ to indicate braking (block 27); the transmission sensor $S_6$ to indicate high vehicle speed or reverse drive (block 28); the proximity sensors $S_7$, $S_8$ at the opposite ends of the vehicle to indicate the proximity of the vehicle to other vehicles (block 29); the darkness sensor $S_9$ (block 30); the rain sensor $S_{10}$ (block 31); and turn-indicator sensors $S_{11}$ (block 32), and other sensors such as vehicle speed.

FIG. 3 illustrates a further input from navigation software (block 33) with which the vehicle may be equipped in order to assist the driver in navigating the vehicle to various desired locations. For example, the navigation software could be pre-programmed to output a signal to microprocessor 20 at certain locations, such as at heavily-trafficked roads, intersections, bridges, tunnels, etc., where the full concentration of the driver is sufficiently critical to avoid distractions as may be caused by a telephone call.

It will be appreciated that other sensors could be provided as inputs into microprocessor 20 wherein similar conditions may occur, either on the part of the driver, the vehicle, and/or the environment, in which, for purposes of safety, external distractions are to be avoided such as may be caused by making or receiving a telephone call.

In the preferred embodiment of the invention, the microprocessor 20, among other functions, acts as a "state machine" to define, arrange and prioritize features and functionalities of the system. In other applications this function can be performed by standalone which interconnects with a microprocessor 20. The state machine aspect of the microprocessor may make telematic control decisions on a variety of criteria such as: (a) the frequency of use of the application, the frequency in which a number, e-mail or URL is contacted; (b) based on safety/urgency priorities, e.g. cruise or CD changer, cell messages or other telematics, or music played on the radio; (c) as preset by the operator; (d) optionally, based on other collected information from the driving system, the microprocessor will initiate calls at predetermined times out of voice mail as, for example, when the driver completes backing out of a driveway and begins a trip.

The user provides signals to the state machine to block features or incoming telematics based on ID, location of phone numbers, e-mail addresses or URL. The blocked or stored telematics will be announced to the driver or stored for use in controlling the system in the future.

The state machine employs an assessment of the incoming cells and places them in categories such as: (a) likely and/or known to cause distraction and accidents; (b) likely but not known to cause distraction and accidents; (c) may cause distraction or accidents; (d) not likely and not known to cause distraction and accidents. These categories will be used to determine the effect of the incoming signals on the telematic system in accordance with the following Table 1:

TABLE 1

Device/Feature assessment.
Copyright © 1982–2002 Applikompt,
Applied Computer Technologics, Inc.

| Categories | | Rank | | | |
|---|---|---|---|---|---|
| Effect | | A | B | C | D |
| 1 Likely AND/OR Known to cause distraction AND accidents | | X | ? | ? | ? |
| 2 Likely BUT NOT Known to cause distraction AND accidents | | ? | X | ? | ? |
| 3 May Cause distraction or accident | | ? | ? | X | ? |
| 4 NOT Likely AND NOT Known to cause Distraction AND Accident | | ? | ? | ? | X |

Application usage Assessment
Copyright © 1987–2002

| 01-Clearly separating what's: | 1 a-Important for safe driving | Class A |
|---|---|---|
| | 1a.1-Subject Vehicle | Class A–S |
| | 1a.2-Other Vehicles | Class A–O |
| | 1 b - Important to drivers | Class B |
| | 1 c - "Nice to Have" for drivers | Class C |
| | 1 d - "Important/Nice to Have" for Passengers | Class D |

User interface requirement Assessment
Copyright © 1987–2002

| 02-Assuring driver intent | Class A |
|---|---|
| 03: Simplicity | Class A |
| 04: Accessibility | Class A |
| 05: High Availability | Class B |
| 06: Universality | Class B |

Self customization/individualization requirement Assesment

| 07: Portability | Class B |
|---|---|
| 08: adaptive | Class A |
| 09: Privacy | Class B |

Owner requirement Assesment

| 10: Cost | Class C |
|---|---|
| 11: Interchangeability | Class A |

Classification A B or C need to be addressed. D can be totally ignored.

The outputs from microprocessor 20 include control signals as shown by the following blocks: block 41, effective to disable the telephone or other telematics from making outgoing calls; block 42, effective to disable the telephone from receiving incoming calls and from actuating the ringing signal; block 43, effective to disable the computer, if provided, from accessing the Internet to make or receive e-mail, faxes, etc.; block 44, effective to actuate a visual indicator viewable by the driver; and block 45, effective to actuate an audible alarm.

Operation

Figure 4:
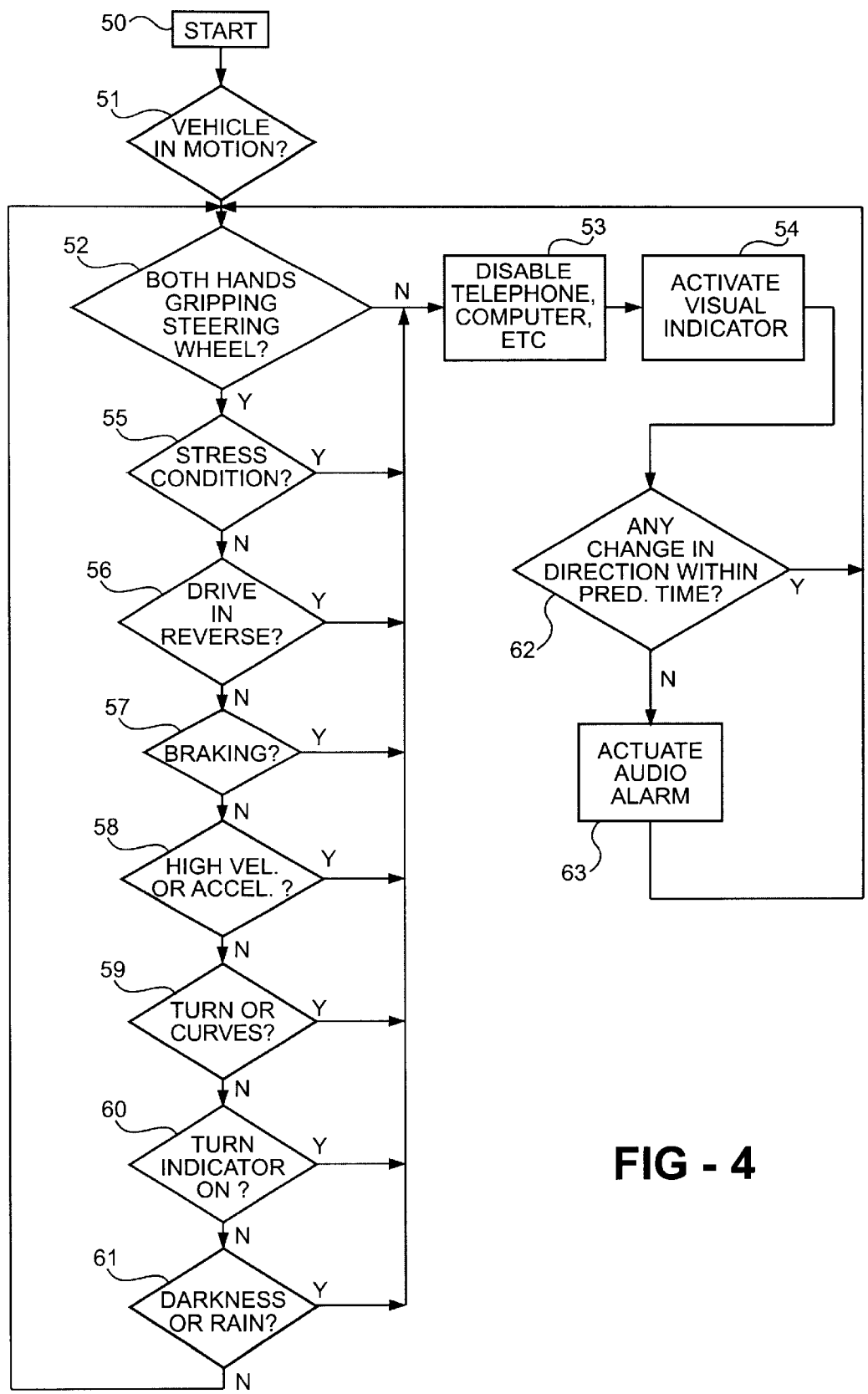
FIG. 4 is a flowchart illustrating the operation of the system of FIG. 1.
Figure 5:
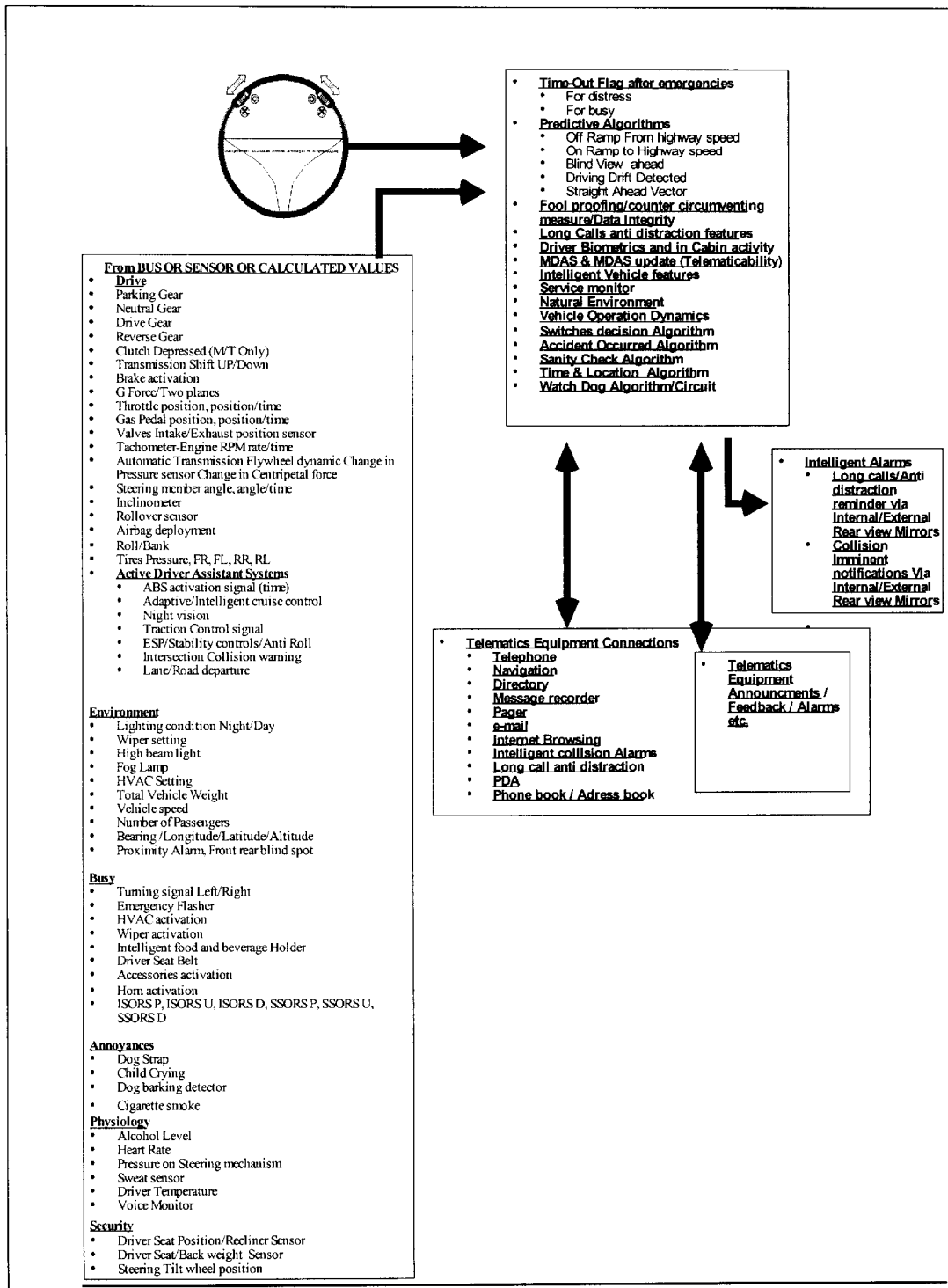
FIG. 5 is a block diagram illustrating the nature and the flow of signals in the system of the present invention.

FIG. 4 is a flowchart illustrating an example of the operation of the system of FIGS. 1–3.

Thus, as shown in FIG. 4, the control system is made operational when the vehicle is in motion (blocks 50, 51). When the vehicle is in motion, a microprocessor 20 outputs signals 41, 42 and 43 (FIG. 3) disabling the vehicle telephone, computer, etc. within the vehicle (block 53), and also signal 44 actuating a visual indicator within the vehicle to indicate this condition (block 54).

If, on the other hand, both hands of the driver are properly gripping the steering wheel 4 so as to actuate the two sensors $S_1$, $S_2$, one or both of the sensors is used to sense a physiological condition of the driver that might indicate a stress condition (block 55). For example, such a stress condition could be indicated by an unduly high gripping force applied by one or both of the hands of the driver to the steering wheel, or by an unduly high pulse rate of the driver or skin conductivity of the driver indicating a high degree of perspiration. If such a stress condition is indicated as being present, the telephone, computer, etc. are also disabled (block 53), and a visual indicator activated (block 54) to indicate this condition.

Next, the system checks to determine the condition of the vehicle, e.g. whether the vehicle: is traveling in reverse, as indicated by sensor $S_6$ (block 56); is being braked, as indicated by sensor $S_5$ (block 57); is traveling at or over a predetermined high velocity or high acceleration, as indicated by sensor $S_6$ (block 58); is executing a curve or turn, as indicated by steering mechanism sensor $S_3$ (block 59); is about to execute a turn, as indicated by turn indicator sensor $S_{11}$ (block 60); or is traveling in the dark or in the rain, as indicated by sensor $S_9$ or sensor $S_{10}$ (block 61). If any of these conditions is sensed, the telephone and the Internet access by the computer are also disabled (block 53), and a visual indicator is actuated to indicate this condition (block 54).

As further shown in FIG. 4, if while the vehicle is in motion no change in steering direction has been sensed within a predetermined time interval (block 62), an audio alarm or vibrator is also activated (block 63) to alert the driver to a possible drowsiness or dozing condition. Other alarms to overcome driver drowsiness would include vibration in the seat, changing HVAC temperature settings and/or blower speed to extremes, etc.

If desired, a manual override switch can be provided to enable the driver to manually override any of these controls, preferably except for the control of block 52 assuring that both hands of the driver are properly gripping the steering wheel.

Setup Scenario:

Driver set up a portable Telematic device such as a cell phone, or a web page etc. With driver preferences:
(1) Control preferences, e.g. Hands always Vs Hands on for Telematics only
(2) Annoyance items: Baby crying, Dog barking, smokers in car etc.
(3) Telematics option: Preferred application to use, preferred priority system etc.
(4) Other emergency and identifying information.
(5) A driver enters a vehicle
   a. docks all electronic communication equipment, e.g. pager, cell phone, PDA, etc., to the control system wirelessly or physically, thus identifies him/herself to the vehicle
   b. System mutes all Telematics but keeps them active
   c. Driver initiates his/her trip.

Scenario One (Driver Initiated)

The driver wants to make a call, review pages, read e-mail or connect to the Internet. (1) The driver will activate the safety switch and then, after the system acknowledges safety switch activation by providing the driver with a beep or voice feedback, the driver with his/her hand on the actuated safety switch will toggle through options with the toggle switch until he gets to a selection that is needed, then using the toggle switch will confirm selection and proceed with the desired action. This could be multiple layers of options.

These options can be provided on a HUD or via voice. Even if devices can be activated by voice control, they still need to have the safety switch depressed to ensure driver intention and not an erroneous sound from the radio or a passenger or a malfunction of devices. During this time the driver's hands must remain at 10/10. The driver must maintain the steering wheel within a specific angle which is calculated based on the following inputs: (1) weather condition, (2) speed of vehicle, (3) proximity of vehicle to others (front/back), feedback from ABS, ESP, traction control, etc. This angle (for example) is about 30 degrees either side of zero if the speed is 40 mph, but it is less when the speed is higher and more when the speed is lower. The driver will also be allowed to temporarily take his hands off the 10/10 position to, for example, make a sharp turn but will have to put them back at 10/10 to continue the previous activity. This amount of time is again dependent on speed, weather, vehicle proximity to others and feedback from ABS, ESP and traction control.

Scenario Two (Incoming)

Incoming information will be customized by the driver, in accordance with Table A, to select what he/she wants to receive and in what priority. Once incoming information is detected by the system, the system will go through a checklist to verify feedback from steering about position and about speed and ABS and ESP and traction control and weather condition. When all conditions are met, the system will announce the incoming information to the driver who will have to press the safety control switch and hold up. While using the toggle switch to accept the incoming information, the remainder of the controls will be as per outgoing, including hands at 10/10 and hands off for a certain temporary amount of time.

It will thus be seen that the illustrated system is effective to disable the operation of the telephone (and/or access to the Internet by a computer) within the vehicle when any of the above-described conditions is sensed, to thereby avoid a distraction which may cause accidents. The fact that both hands of the driver must be gripping the steering wheel in order to enable the operation of the telephone (and/or computer) not only requires that the vehicle must be equipped with a "hands free" capability, but that the driver must actually use this "hands free" capability created by the system gateway in order to make or receive telephone calls or other telematics activities. In addition, other sensors could also be provided to disable a vehicle telephone or a multi-function telematics system or Internet access provided by a vehicle computer in response to other conditions, such as the detection within the vehicle of the sounds of an emergency siren in an approaching vehicle, a child crying within the vehicle, the driver use of a drink from a monitored cup holder or a monitored food tray, or the activities such as modifying the cabin temperature, changing the volume on the radio, extending the sun visor etc.

The monitoring of all such signals, sensors, data and conditions is done by a modular dynamic plug and play state machine that integrates, prioritizes, enables, blocks or mutes telematics application and telematics functionalities based on priorities determined by learning frequency and characteristics of use or by driver preset preferences.

Such machine may be a hardware based, a software embedded in a dedicated hardware or a software/protocol embedded in one or more telematic equipment and it may act as a node on a network of telematic equipment and the vehicle bus, or as a hub for all telematics and a gateway to the vehicle, or any combination of the above.

The state machine can allow driver to set their preferences on a portable telematics device such as a cellular phone, or a WAN, Web site or via a FTP and e-mail. Such set up can be transferred to the vehicle in use when the driver docks the cell phone or other portable telematics devices to the system gateway. The downloaded profile will be updated with driving skills, driver habits and geographical/time/date based notes added by the driver while driving. The updated profile will be uploaded back to the source when the vehicle comes to a final stop, or ongoing as driving is being carried out. Such data may be direct values and status or a statistical representation of a driving experience.

The preferences included by the driver will range from telematics management options, e.g. preset priorities or automatic based on learning by frequency of use, tags of time, location and physiology. Preset priorities will allow a driver to assign sequence of access to telematics and telematics functionalities or to block certain activities based on time of day or source of telematics or geography at will. Automatic based learning condition, on the other hand, for example, if the driver physiology shows stress during a telephone conversation with a certain number, such number will be tagged and will be treated as a source of high risk and will be blocked during unusually risky conditions so a driver does not engage in additional cognitive hungry activities. Additionally, if a driver uses telematics device A more often the B which is used less often then C, the access to such devices will be based on the mostly used first. In this case, A is followed by C and C is followed by B. Similar frequency based access priorities are applied to function of such telematics and also prioritized based on time, geography etc.

Other preferences set by the driver can include emergency contacts, medical record summary or identification, etc. to be used along with telemetry data when automatically reporting an accident via text to speech and via e-mail. This will help emergency dispatch understand and prepare the correct type of help needed, e.g. number of passengers, fire in cabin, impact speed, driver physiology and the driving telemetry before and during the impact.

The decisions to block, enable etc are accomplished by algorithms that share the hosts of signals provided to monitor for specific conditions that portrays. These algorithms also update the driver profile to include skills and habits for further relaxing or restricting telematics. For example, a driver that drives frequently on expressways and in close proximity to other vehicles will be allowed more leeway then a person that hardly drives on the expressway. Similar monitoring occurs for nighttime driving, adverse weather driving and so on.

While it will be appreciated, therefore, that while the invention has been described with respect to one preferred embodiment, many other variations, modifications and applications of the invention may be made.

What is claimed is:

1. A safety control system for vehicles including a telematics device and sensor means for sensing a potentially dangerous condition and for automatically disabling use of the telematics device when sensing such condition; characterized in that said sensor means includes two sensors mounted on a steering member to be gripped by the two hands of the driver of the vehicle and effective to suspend or disable the telematics device when the two hands of the driver are not sensed as gripping said steering member while the vehicle is in motion.

2. The system according to claim 1, wherein said telematics device comprises a telephone.

3. The system according to claim 1, wherein said steering member is a steering wheel, and said sensor means includes two sensors on opposite sides of said steering wheel located to sense the proper gripping of the steering wheel by the two hands of the driver.

4. The system according to claim 1, wherein said two sensors are located approximately on or between the "two" and "ten" and the "three and "nine" clock positions of the steering wheel.

5. The system according to claim 1, wherein said vehicle further comprises a computer or multifunction telematics device allowing access to the Internet for transmitting and/or receiving faxes or e-mail, WAN or browsing websites, and wherein said sensor means disables said access when the two hands of the driver are not sensed as gripping the steering member while the vehicle is in motion and the risky dangerous conditions are taking place.

6. The system according to claim 1, wherein said system is monitored by a dynamic modular plug and play learning state machine.

7. The system according to claim 6, wherein said state machine receives data constituting a profile in statistical format or raw format from portable telematics devices or other data mediums including Web sites, FTP, e-mail WAN, coded tones via cellular calls.

8. The system according to claim 6, wherein said state machine updates data in statistical format or raw format to portable telematics devices or other data mediums including Web sites, FTP, e-mail WAN, coded tones via cellular calls.

9. The system according to claim 6, wherein said state machine uploads and stores data in statistical format or raw format to portable telematics devices or other data mediums including Web sites, FTP, e-mail WAN, coded tones via cellular calls.

10. The system according to claim 1, wherein said sensor means further includes a reverse-drive condition sensor for sensing when the vehicle is moving in reverse, and wherein said latter sensor also disables said telematics when sensing said reverse-drive condition of the vehicle.

11. The system according to claim 1, wherein said sensor means further includes a braking sensor.

12. The system according to claim 1, wherein said sensor means also includes a velocity sensor for sensing a high velocity of the vehicle, and wherein said velocity sensor also disables said telephone when sensing the vehicle being driven at an unduly high velocity.

13. The system according to claim 1, wherein said vehicle further includes a signaling device, and wherein said sensor means also actuates said signaling device when risky dangerous conditions are taking place.

14. The system according to claim 1, wherein at least one of said sensors sensing a hand when gripping the steering member also senses a physiological condition of the driver and also disables the telephone when a predetermined physiological condition is sensed and/or risky dangerous conditions are taking place.

15. The system according to claim 14, wherein said physiological condition is a predetermined gripping force applied by at least one of the hands of the driver while gripping said steering member.

16. The system according to claim 14, wherein said physiological condition is a predetermined pulse rate, temperature, and/or skin conductivity of the driver as sensed from at least one of the hands of the driver while gripping said steering member.

17. The system according to claim 14, wherein said vehicle includes an alarm, and said sensor means actuates said alarm when sensing a predetermined physiological condition indicating drowsiness in the driver.

18. The system according to claim 14, wherein said sensor means further includes a steering direction sensor, and also actuates said alarm when sensing a failure to change the steering direction within a predetermined time, and distance interval relative to speed indicating a possible drowsiness condition in the driver.

19. The system according to claim 1, wherein said sensor means further includes a monitoring of headlight, fog light and wipers, and wherein said latter sensor also disables said telephone when sensing darkness or rain darkness and or rain are coupled with other conditions that will make driving dangerous or increased risk.

20. A safety system for vehicles having a telephone, a drive including an engine or electric motor and a transmission/or other torque conversion device for driving the vehicle, a steering mechanism including a steering member for steering the vehicle, a plurality of signaling devices for signaling the driver as to various conditions of the vehicle, and a control system including sensor means for sensing potentially dangerous conditions and for controlling the vehicle and said plurality of signaling devices;

characterized in that said sensor means includes first and second sensors mounted on said steering member to be gripped by the two hands of the driver of the vehicle and effective to disable an operation of said telephone when the two hands of the driver are not sensed as gripping said steering member while the vehicle is in motion and the risky dangerous conditions are taking place.

21. The system according to claim 20, wherein said steering member is a steering wheel and said first and second sensors are located approximately on or between the "two" and "ten" and the "three" and "nine" clock positions of the steering wheel or other steering components.

22. The system according to claim 20, wherein said first and second sensors also actuate at least one of said signaling devices when the two hands of the driver are not sensed as gripping the steering member.

23. The system according to claim 20, wherein at least one of said first and second sensors also senses a physiological condition of the driver and also disables said telephone when a predetermined physiological condition is sensed.

24. The system according to claim 23, wherein said physiological condition sensed by at least one of said first and second sensors is a predetermined gripping force applied by the respective hand of the driver while gripping said steering member.

25. The system according to claim 23, wherein said physiological condition sensed by at least one of the first and second sensors is a predetermined pulse rate, temperature, and/or skin conductivity of the respective hand of the driver.

26. The system according to claim 23, wherein said first and second sensors actuate at least one of said sensing devices when sensing a predetermined physiological characteristic indicating drowsiness or stress in the driver.

27. The system according to claim 23, wherein at least one of said signaling devices is an audio alarm; and wherein said first and second sensors actuate said audio alarm when a drowsiness condition is sensed.

28. The system according to claim 20, wherein said sensor means further includes a steering direction sensor, and also actuates said alarm when sensing a failure to change the steering direction within a predetermined time interval indicating a possible drowsiness condition in the driver.

29. The system according to claim 20, wherein said vehicle also includes a computer allowing access to the Internet for transmitting and/or receiving faxes or e-mail;

and wherein said first and second sensors disable said access when the two hands of the driver are not sensed as gripping said steering member while the vehicle is in motion.

30. The system according to claim 20, wherein said sensor means includes a drive sensor for sensing the reverse-drive condition of the vehicle; and wherein said drive sensor also disables said telephone when sensing the reverse-drive condition of the vehicle.

31. The system according to claim 20, wherein said sensor means includes a braking sensor for sensing the braking condition of the vehicle; and wherein said system disables said telephone when sensing the vehicle being braked.

32. The system according to claim 20, wherein said sensor means includes a vehicle-proximity sensor for sensing proximity to other vehicles; and wherein said vehicle-proximity sensor also disables said telephone when sensing another vehicle within a predetermined proximity.

33. The system according to claim 20, wherein said sensor means includes a velocity sensor for sensing a high velocity of the vehicle; and wherein said velocity sensor also disables said telephone when sensing the vehicle traveling at a high velocity.

34. A method of avoiding potentially dangerous conditions while operating a vehicle having a telephone and a steering mechanism including a steering member to be manipulated by the driver, comprising:

providing the steering member with two sensors for sensing the gripping of the steering member by the two hands of the driver;

and disabling an operation of said telephone when the two sensors fail to sense the gripping of the steering member by both hands of the driver while the vehicle is in motion.

35. The method according to claim 34, wherein said telephone is also disabled when the vehicle is traveling in the reverse direction.

36. The method according to claim 34, wherein said telephone is also disabled when the vehicle is in motion and is sensed by a proximity sensor to be within a predetermined distance from another vehicle.

37. The method according to claim 34, wherein said telephone is also disabled when the vehicle is traveling at a velocity above a predetermined value.

38. The method according to claim 34, wherein a signaling device in the vehicle is also actuated when the gripping of the steering member by both hands of the driver is not sensed.

39. The method according to claim 34, wherein at least one of said sensors also senses a physiological condition of the driver and disables said telephone when a predetermined physiological condition is sensed.

40. The method according to claim 39, wherein said predetermined physiological condition is a predetermined gripping force applied by the respective hand of a driver indicating a stress condition in the driver while gripping said steering member.

41. The method according to claim 39, wherein said predetermined physiological condition is a predetermined pulse rate, temperature, or skin conductivity of the respective hand of the driver indicating a stress condition in the driver while gripping said steering member.

42. The method according to claim 39, wherein said sensors actuate an audible alarm when the sensed physiological condition is such as to indicate a possible drowsiness condition in the driver.

43. The method according to claim 39, wherein said sensors actuate a visual indicator when the sensed physiological condition is such as to indicate a possible stressed condition in the driver.

44. The method according to claim 34, wherein the steering direction of the vehicle is also sensed, and an audible alarm is actuated when the steering direction has not been changed within a predetermined time interval such as to indicate a possible drowsiness condition in the driver.

45. The system according to claim 1 wherein the steering wheel has spokes and at least one of said sensors is mounted on the spokes.

* * * * *